(12) United States Patent
Wang et al.

(10) Patent No.: US 12,084,726 B2
(45) Date of Patent: Sep. 10, 2024

(54) **DETECTION KIT FOR *Salmonella typhi*, PREPARATION METHOD AND APPLICATION THEREOF**

(71) Applicants: Weijia Wang, Zhongshan (CN); Yong Yuan, Zhongshan (CN)

(72) Inventors: Weijia Wang, Zhongshan (CN); Qian Dong, Zhongshan (CN); Kang Chen, Zhongshan (CN); Xinjie Wang, Zhongshan (CN); Peng Liu, Zhongshan (CN); Jinye Xie, Zhongshan (CN); Yang Li, Zhongshan (CN); Yiyun Geng, Zhongshan (CN); Xinyi Liu, Zhongshan (CN); Juan Wang, Zhongshan (CN); Yanping Feng, Zhongshan (CN)

(73) Assignees: Weijia Wang, Zhongshan (CN); Yong Yuan, Zhongshan (CN)

( * ) Notice: Subject to any disclaimer, the term of this patent is extended or adjusted under 35 U.S.C. 154(b) by 0 days.

(21) Appl. No.: 18/023,739

(22) PCT Filed: Feb. 22, 2022

(86) PCT No.: PCT/CN2022/077255
§ 371 (c)(1),
(2) Date: Feb. 28, 2023

(87) PCT Pub. No.: WO2022/179494
PCT Pub. Date: Sep. 1, 2022

(65) Prior Publication Data
US 2024/0084402 A1    Mar. 14, 2024

(30) Foreign Application Priority Data
Feb. 26, 2021  (CN) .......................... 202110215553.9

(51) Int. Cl.
C07H 21/02        (2006.01)
C12Q 1/6806     (2018.01)
C12Q 1/689       (2018.01)

(52) U.S. Cl.
CPC .......... *C12Q 1/689* (2013.01); *C12Q 1/6806* (2013.01)

(58) Field of Classification Search
USPC .................. 435/6.1, 6.11, 91.1; 436/94, 501; 536/23.1, 24.3, 24.33
See application file for complete search history.

(56) References Cited

FOREIGN PATENT DOCUMENTS

CN        110684823 Y        1/2020

OTHER PUBLICATIONS

Massi, M.N. et al., "Quantitative detection of *Salmonella enterica* serovar Typhi from blood of suspected typhoid fever patients by real-time PCR", International Journal of Medical Microbiology, vol. 295, No. 2, Jun. 30, 2005 (Jun. 30, 2005).

(Continued)

*Primary Examiner* — Frank W Lu
(74) *Attorney, Agent, or Firm* — Zhigang Ma

(57) ABSTRACT

The present disclosure discloses a detection kit for *Salmonella typhi*, a preparation method and an application thereof, the detection kit includes: amplification primer, crRNA, LbCas12a-RR protein and a single-stranded DNA reporting system, the crRNA is a specific crRNA for a detection segment of the flag gene of *Salmonella typhi*; a LbCas12a-RR protein expression sequence is a prokaryotic codon optimized with a Cas12 protein nucleic acid sequence, and amino acid positions of 532 and 595 are mutated into G532R and K595R, respectively. The application of the kit is, to use the detection kit of *Salmonella typhi* for nucleic acid detec- (Continued)

tion of *Salmonella typhi*; and the kit has high sensitivity, high specificity and fast visualization.

3 Claims, 6 Drawing Sheets

Specification includes a Sequence Listing.

(56) References Cited

OTHER PUBLICATIONS

Gao, Linyi et al., "Engineered Cpf1 variants with altered PAM specificities", Nat Biotechnol, vol. 35, No. 8, Jun. 5, 2017 (Jun. 5, 2017).

```
                        SEQUENCE LISTING

<160> NUMBER OF SEQ ID NOS: 32

<210> SEQ ID NO 1
<211> LENGTH: 36
<212> TYPE: DNA
<213> ORGANISM: synthetic construct
<220> FEATURE:
<223> OTHER INFORMATION: amplification primer

<400> SEQUENCE: 1
tctccattgc gcagaccact gaaggcgcgc tgaacg                         36

<210> SEQ ID NO 2
<211> LENGTH: 31
<212> TYPE: DNA
<213> ORGANISM: synthetic construct
<220> FEATURE:
<223> OTHER INFORMATION: amplification primer

<400> SEQUENCE: 2
tttcggggtg taggcatctt ggacattaag c                              31

<210> SEQ ID NO 3
<211> LENGTH: 27
<212> TYPE: DNA
<213> ORGANISM: synthetic construct
<220> FEATURE:
<223> OTHER INFORMATION: amplification primer

<400> SEQUENCE: 3
tctgcgaatg gtactaactc ccagtct                                   27

<210> SEQ ID NO 4
<211> LENGTH: 27
<212> TYPE: DNA
<213> ORGANISM: synthetic construct
<220> FEATURE:
<223> OTHER INFORMATION: amplification primer

<400> SEQUENCE: 4
tttaaaagaa atcagctcta aaacact                                   27

<210> SEQ ID NO 5
<211> LENGTH: 1297
<212> TYPE: DNA
<213> ORGANISM: Salmonella
<220> FEATURE:
<223> OTHER INFORMATION: Salmonella typhi

<400> SEQUENCE: 5
atggcacaag tcattaatac aaacagcctg tcgctgttga cccagaataa cctgaacaaa    60
tcccagtccg cactgggcac tgctatcgag cgtttgtctt ccggtctgcg tatcaacagc   120
gcgaaagacg atgcggcagg acaggcgatt gctaaccgtt ttaccgcgaa catcaaaggt   180
ctgactcagg cttcccgtaa cgctaacgac ggtatctcca ttgcgcagac cactgaaggc   240
gcgctgaacg aaatcaacaa caacctgcag cgtgtgcgtg aactggcggt tcagtctgcg   300
aatggtacta actcccagtc tgacctcgac tccatccagg ctgaaatcac ccagcgcctg   360
aacgaaatcg accgtgtatc cggccagact cagttcaacg gcgtgaaagt cctggcgcag   420
```

```
gacaacaccc tgaccatcca ggttggtgcc aacgacggtg aaactatcga tattgattta    480
aaagaaatca gctctaaaac actgggactt gataagctta atgtccaaga tgcctacacc    540
ccgaaagaaa ctgctgtaac cgttgataaa actacctata aaaatggtac agatcctatt    600
acagcccaga gcaatactga tatccaaact gcaattggcg gtggtgcaac gggggttact    660
ggggctgata tcaaatttaa agatggtcaa tactatttag atgttaaagg cggtgcttct    720
gctggtgttt ataaagccac ttatgatgaa actacaaaga aagttaatat tgatacgact    780
gataaaactc cgttggcaac tgcggaagct acagctattc ggggaacggc cactataacc    840
cacaaccaaa ttgctgaagt aacaaaagag ggtgttgata cgaccacagt tgcggctcaa    900
cttgctgcag caggggttac tggcgccgat aaggacaata ctagccttgt aaaactatcg    960
tttgaggata aaaacggtaa ggttattgat ggtggctatg cagtgaaaat gggcgacgat   1020
ttctatgccg ctacatatga tgagaaaaca ggtgcaatta ctgctaaaac cactacttat   1080
acagatggta ctggcgttgc tcaaactgga gctgtgaaat tggtggcgc aaatggtaaa   1140 tctgaagttg ttactgctac cgatggtaag acttacttag caagcgacct tgacaaacat   1200
aacttcagaa caggcggtga gcttaaagag gttaatacag ataagactga aaacccactg   1260
cagaaaattg atgctgcctt ggcacaggtt gatacac                            1297

<210> SEQ ID NO 6
<211> LENGTH: 3744
<212> TYPE: DNA
<213> ORGANISM: synthetic construct
<220> FEATURE:
<223> OTHER INFORMATION: LbCas12a-RR protein

<400> SEQUENCE: 6
agcaagctgg aaaaatttac caactgctac agcctgagca agaccctgcg tttcaaagcg     60
atcccggttg gcaagaccca ggaaaacatt gacaacaaac gtctgctggt tgaggacgaa    120
aagcgtgcgg aggattataa aggtgtgaag aaactgctgg atcgttacta tctgagcttt    180
atcaacgacg tgctgcacag cattaagctg aaaaacctga caactacat cagcctgttc    240 cgtaagaaaa cccgtaccga aaggaaaac aaagagctgg aaaacctgga atcaacctg     300 cgtaaggaga ttgcgaaggc gttcaagggt aacgagggct acaagagcct gttcaagaaa    360
gatatcatcg aaaccatcct gccggagttc ctggacgata aggacgaaat tgcgctggtt    420
aacagcttca acgttttttac caccgcgttc accggcttct ttgataaccg tgagaacatg    480
tttagcgagg aagcgaaaag caccagcatc gcgttccgtt gcattaacga aaacctgacc    540
cgttacatca gcaacatgga cattttcgag aaggttgacg cgatctttga taaacacgag    600
gtgcaggaaa tcaaggagaa aattctgaac agcgactatg atgttgaaga tttctttgag    660
ggtgaattct ttaactttgt tctgacccaa gagggcatcg acgtgtacaa cgcgatcatt    720
ggtggcttcg tgaccgaaag cggcgagaag atcaaggcc tgaacgagta cattaacctg    780
tataaccaga gaccaaaca aaagctgccg aaatttaagc gcctgtataa gcaggtgctg    840
agcgatcgtg aaagcctgag cttctacggc gagggctata ccagcgacga ggaagttctg    900
gaagtgtttc gtaacaccct gaacaaaaac agcgagatct tcagcagcat taagaaactg    960
gaaaagctgt tcaaaaactt tgacgagtac agcagcgcgg gtatctttgt taagaacggc    1020
ccggcgatca gcaccattag caaagatatc ttcggtgaat ggaacgtgat tcgtgacaag    1080
tggaacgcgg agtatgacga tatccacctg aagaaaaagg cggtggttac cgaaaagtac   1140
gaggacgatc gtcgtaaaag cttcaaaaag attggcagct ttagcctgga acagctgcaa    1200
```

```
gagtacgcgg acgcggatct gagcgtggtt gaaaaactga aggagatcat tatccagaag   1260
gttgatgaaa tctacaaagt gtatggtagc agcgagaagc tgttcgacgc ggattttgtt   1320
ctggagaaga gcctgaaaaa gaacgacgcg gtggttgcga tcatgaagga cctgctggat   1380
agcgtgaaaa gcttcgaaaa ctacattaag gcgttctttg gtgaaggcaa agagaccaac   1440
cgtgacgaga gcttctatgg cgattttgtt ctggcgtacg acatcctgct gaaggtggac   1500
cacatctacg atgcgattcg taactatgtt acccaaaaac cgtacagcaa ggataagttc   1560
aagctgtact ccagaaccc gcaattcatg cgtggctggg acaaggataa agagaccgac   1620
tatcgtgcga ccatcctgcg ttacggtagc aagtactatc tggcgattat ggataaaaag   1680
tacgcgaaat gcctgcagaa gatcgacaaa gacgatgtta acggtaacta cgaaaagatc   1740
aactacaagc tgctgccggg cccgaacaag atgctgccgc gagtgttctt tagcaaaaag   1800
tggatggcgt actataaccc gagcgaggac atccaaaaga tctacaagaa cggtaccttc   1860
aaaaagggcg atatgtttaa cctgaacgac tgccacaagc tgatcgactt ctttaaagat   1920
agcattagcc gttatccgaa gtggagcaac gcgtacgatt tcaactttag cgagaccgaa   1980
aagtataaag acatcgcggg tttttaccgt gaggttgagg aacagggcta taaagtgagc   2040
ttcgaaagcg cgagcaagaa agaggtggat aaactggtgg aggaaggtaa actgtacatg   2100
ttccaaatct acaacaagga cttcagcgat aagagccacg gcaccccgaa cctgcacacc   2160
atgtacttca agctgctgtt tgacgaaaac aaccatggtc agatccgtct gagcggtggc   2220
gcggagctgt tcatgcgtcg tgcgagcctg aagaaagagg agctggttgt gcacccggcg   2280
aacagcccga ttgcgaacaa aaacccggat aacccgaaaa agaccaccac cctgagctac   2340
gacgtgtata aggataaacg ttttagcgaa gaccaatacg agctgcacat tccgatcgcg   2400
attaacaagt gcccgaaaaa catcttcaag attaacaccg aagttcgtgt gctgctgaaa   2460
cacgacgata cccgtatgt tatcggtatt gaccgtggcg agcgtaacct gctgtacatc   2520
gtggttgtgg acggtaaagg caacattgtg gaacagtata gcctgaacga gattatcaac   2580
aactttaacg gtatccgtat taagaccgat taccacagcc tgctggacaa aaaggagaag   2640
gaacgtttcg aggcgcgtca gaactggacc agcatcgaaa acattaagga gctgaaagcg   2700
ggctatatca gccaagttgt gcacaagatt tgcgaactgg ttgagaaata cgatgcggtg   2760
atcgcgctgg aggacctgaa cagcggtttt aagaacagcc gtgttaaggt ggaaaagcag   2820
gtttaccaaa agttcgagaa gatgctgatc gataagctga actacatggt ggacaaaaag   2880
agcaacccgt gcgcgaccgg tggcgcgctg aaaggttatc agattaccaa caagttcgaa   2940
agctttaaaa gcatgagcac ccaaaacggc ttcatctttt acattccggc gtggctgacc   3000
agcaaaatcg atccgagcac cggttttgtt aacctgctga gaccaaata taccagcatt   3060 gcggatagca aaaagttcat cagcagcttt gaccgtatta tgtacgtgcc ggaggaagac   3120
ctgttcgagt ttgcgctgga ctataagaac ttcagccgta ccgacgcgga ctacatcaaa   3180
aagtggaaac tgtacagcta tggtaaccgt atccgtattt ccgtaacccc gaaaaagaac   3240
aacgtttttg actgggagga agtgtgcctg accagcgcgt ataaggaact gttcaacaaa   3300
tacggtatca actatcagca aggcgatatt cgtcgcgctgc tgtgcgagca gagcgacaag   3360
gcgttctaca gcagctttat ggcgctgatg agcctgatgc tgcaaatgcg taacagcatc   3420
accggtcgta ccgatgttga ttttctgatc agcccggtga aaacagcga cggcattttc   3480 tacgatagcc gtaactatga agcgcaggag aacgcgattc tgccgaagaa cgcggacgcg   3540
```

```
aacggtgcgt ataacatcgc gcgtaaagtt ctgtgggcga ttggccagtt caaaaaggcg      3600
gaggacgaaa agctggataa ggtgaaaatc gcgattagca acaaagaatg gctggagtac      3660
gcgcaaacca gcgttaagca cgagaacctg tacttccaat cccaccacca ccaccaccac      3720
caccaccacc accaccacca ctga                                             3744
```

<210> SEQ ID NO 7
<211> LENGTH: 26
<212> TYPE: DNA
<213> ORGANISM: synthetic construct
<220> FEATURE:
<223> OTHER INFORMATION: amplification primer

<400> SEQUENCE: 7

```
ggcacaagtc attaatacaa acagcc                                             26
```

<210> SEQ ID NO 8
<211> LENGTH: 24
<212> TYPE: DNA
<213> ORGANISM: synthetic construct
<220> FEATURE:
<223> OTHER INFORMATION: amplification primer

<400> SEQUENCE: 8

```
gaagtgtatc aacctgtgcc aagg                                               24
```

<210> SEQ ID NO 9
<211> LENGTH: 27
<212> TYPE: DNA
<213> ORGANISM: synthetic construct
<220> FEATURE:
<223> OTHER INFORMATION: amplification primer

<400> SEQUENCE: 9

```
tcttttaaat caatatcgat agtttca                                            27
```

<210> SEQ ID NO 10
<211> LENGTH: 27
<212> TYPE: DNA
<213> ORGANISM: synthetic construct
<220> FEATURE:
<223> OTHER INFORMATION: amplification primer

<400> SEQUENCE: 10

```
ttttagagct gatttctttt aaatcaa                                            27
```

<210> SEQ ID NO 11
<211> LENGTH: 25
<212> TYPE: DNA
<213> ORGANISM: synthetic construct
<220> FEATURE:
<223> OTHER INFORMATION: amplification primer

<400> SEQUENCE: 11

```
tttgtcttcc ggtctgcgta tcaac                                              25
```

<210> SEQ ID NO 12
<211> LENGTH: 27
<212> TYPE: DNA
<213> ORGANISM: synthetic construct
<220> FEATURE:
<223> OTHER INFORMATION: amplification primer

<400> SEQUENCE: 12

```
ttttaccgcg aacatcaaag gtctgac                                            27
```

```
<210> SEQ ID NO 13
<211> LENGTH: 27
<212> TYPE: DNA
<213> ORGANISM: synthetic construct
<220> FEATURE:
<223> OTHER INFORMATION: amplification primer

<400> SEQUENCE: 13
tttcacgccg ttgaactgag tctggcc                              27

<210> SEQ ID NO 14
<211> LENGTH: 27
<212> TYPE: DNA
<213> ORGANISM: synthetic construct
<220> FEATURE:
<223> OTHER INFORMATION: amplification primer

<400> SEQUENCE: 14
ttttagcagt aattgcacct gttttct                              27

<210> SEQ ID NO 15
<211> LENGTH: 27
<212> TYPE: DNA
<213> ORGANISM: synthetic construct
<220> FEATURE:
<223> OTHER INFORMATION: amplification primer

<400> SEQUENCE: 15
tttgagcaac gccagtacca tctgtat                              27

<210> SEQ ID NO 16
<211> LENGTH: 27
<212> TYPE: DNA
<213> ORGANISM: synthetic construct
<220> FEATURE:
<223> OTHER INFORMATION: amplification primer

<400> SEQUENCE: 16
tctgcgcaat ggagataccg tcgttag                              27

<210> SEQ ID NO 17
<211> LENGTH: 27
<212> TYPE: DNA
<213> ORGANISM: synthetic construct
<220> FEATURE:
<223> OTHER INFORMATION: amplification primer

<400> SEQUENCE: 17
tctccattgc gcagaccact gaaggcg                              27

<210> SEQ ID NO 18
<211> LENGTH: 27
<212> TYPE: DNA
<213> ORGANISM: synthetic construct
<220> FEATURE:
<223> OTHER INFORMATION: amplification primer

<400> SEQUENCE: 18
tctgacctcg actccatcca ggctgaa                              27

<210> SEQ ID NO 19
<211> LENGTH: 27
<212> TYPE: DNA
<213> ORGANISM: synthetic construct
<220> FEATURE:
```

<223> OTHER INFORMATION: amplification primer

<400> SEQUENCE: 19
tctggccgga tacacggtcg atttcgt                                              27

<210> SEQ ID NO 20
<211> LENGTH: 27
<212> TYPE: DNA
<213> ORGANISM: synthetic construct
<220> FEATURE:
<223> OTHER INFORMATION: amplification primer

<400> SEQUENCE: 20
tctgggctgt aataggatct gtaccat                                              27

<210> SEQ ID NO 21
<211> LENGTH: 27
<212> TYPE: DNA
<213> ORGANISM: synthetic construct
<220> FEATURE:
<223> OTHER INFORMATION: amplification primer

<400> SEQUENCE: 21
tctgtataag tagtggtttt agcagta                                              27

<210> SEQ ID NO 22
<211> LENGTH: 27
<212> TYPE: DNA
<213> ORGANISM: synthetic construct
<220> FEATURE:
<223> OTHER INFORMATION: amplification primer

<400> SEQUENCE: 22
tttgcgccac caaatttcac agctcca                                              27

<210> SEQ ID NO 23
<211> LENGTH: 27
<212> TYPE: DNA
<213> ORGANISM: synthetic construct
<220> FEATURE:
<223> OTHER INFORMATION: amplification primer

<400> SEQUENCE: 23
tttggtggcg caaatggtaa atctgaa                                              27

<210> SEQ ID NO 24
<211> LENGTH: 27
<212> TYPE: DNA
<213> ORGANISM: synthetic construct
<220> FEATURE:
<223> OTHER INFORMATION: amplification primer

<400> SEQUENCE: 24
tttgtcaagg tcgcttgcta agtaagt                                              27

<210> SEQ ID NO 25
<211> LENGTH: 27
<212> TYPE: DNA
<213> ORGANISM: synthetic construct
<220> FEATURE:
<223> OTHER INFORMATION: amplification primer

<400> SEQUENCE: 25
tttaagctca ccgcctgttc tgaagtt                                              27

```
<210> SEQ ID NO 26
<211> LENGTH: 27
<212> TYPE: DNA
<213> ORGANISM: synthetic construct
<220> FEATURE:
<223> OTHER INFORMATION: amplification primer

<400> SEQUENCE: 26
tttctgcagt gggttttcag tcttatc                                   27

<210> SEQ ID NO 27
<211> LENGTH: 34
<212> TYPE: DNA
<213> ORGANISM: synthetic construct
<220> FEATURE:
<223> OTHER INFORMATION: amplification primer

<400> SEQUENCE: 27
tctccattgc gcagaccact gaaggcgcgc tgaa                           34

<210> SEQ ID NO 28
<211> LENGTH: 31
<212> TYPE: DNA
<213> ORGANISM: synthetic construct
<220> FEATURE:
<223> OTHER INFORMATION: amplification primer

<400> SEQUENCE: 28
cctgcagcgt gtgcgtgaac tggcggttca g                              31

<210> SEQ ID NO 29
<211> LENGTH: 33
<212> TYPE: DNA
<213> ORGANISM: synthetic construct
<220> FEATURE:
<223> OTHER INFORMATION: amplification primer

<400> SEQUENCE: 29
aacctgcagc gtgtgcgtga actggcggtt cag                            33

<210> SEQ ID NO 30
<211> LENGTH: 32
<212> TYPE: DNA
<213> ORGANISM: synthetic construct
<220> FEATURE:
<223> OTHER INFORMATION: amplification primer

<400> SEQUENCE: 30
gcagtttctt tcggggtgta ggcatcttgg ac                             32

<210> SEQ ID NO 31
<211> LENGTH: 30
<212> TYPE: DNA
<213> ORGANISM: synthetic construct
<220> FEATURE:
<223> OTHER INFORMATION: amplification primer

<400> SEQUENCE: 31
tcaacggtta cagcagtttc tttcggggtg                                30

<210> SEQ ID NO 32
<211> LENGTH: 32
<212> TYPE: DNA
<213> ORGANISM: synthetic construct
<220> FEATURE:
<223> OTHER INFORMATION: amplification primer
```

-continued

```
<400> SEQUENCE: 32
gcagtttctt tcggggtgta ggcatcttgg ac                                    32
```

DETECTION KIT FOR *Salmonella typhi*, PREPARATION METHOD AND APPLICATION THEREOF

CROSS-REFERENCE TO RELATED APPLICATION

This patent application is a national stage application filed under 35 U.S.C. 371, of International Application No. PCT/CN2022/077255, filed Feb. 22, 2022, which claims priority to, and the benefit of CN113249499A, filed Feb. 26, 2021, the disclosure of which is incorporated by reference herein in its entirety as part of the present application.

REFERENCE TO SEQUENCE LISTING

The substitute sequence listing is submitted as an ASCII formatted text filed via EFS-Web, with a file name of "Substitute_Sequence_Listing_KBJC-U.S. Pat. No. 224,843 P1", a creation date of Oct. 22, 2023, and a size of 12,979 bytes. The substitute sequence Listing filed via EFS-Web is a part of the specification and is incorporated in its entirety by reference herein.

TECHNICAL FIELD

The present disclosure relates to a detection kit for *Salmonella typhi*, a preparation method and an application thereof, and belongs to the technical field of microbial detection.

BACKGROUND

*Salmonella* enterici *typhi* serotype (S. *Typhi*) is a human host-restricted pathogen, and typhoid caused by which is still a major public health problem. It is estimated that about 10.9 million people worldwide are infected with typhoid every year, resulting in nearly 100,000 deaths, with the highest infection rate among children. *Salmonella typhi* is mainly spread by water or food contaminated with feces. When patients ingest contaminated food or water, *Salmonella typhi* will invade intestinal mucosa and spread to the whole body, causing high fever, liver and spleen swelling, skin rash and other acute symptoms. Since the symptoms and signs caused by *Salmonella typhi* are non-specific and difficult to diagnose directly from clinical symptoms, laboratory tests are essential for diagnosis.

At present, the gold standard for the diagnosis of typhoid fever in laboratory is still bacterial isolation and culture, but the positive rate of blood culture is lower than that of bone marrow culture because of the influence of the number of bacteria in blood and the use of antibiotics. However, extraction of bone marrow will increase the risk of infection in the course of diagnosis and treatment, and isolation and culture will take a long time, which is not conducive to early diagnosis. Thus, the most common diagnostic method is the serological Widal test. However, there are serious cross-reactions between this experiment and other infectious pathogens, such as malaria, dengue fever, brucellosis, etc., which tend to produce false positive results and lead to an increase in the rate of misdiagnosis. Moreover, the titres of Widal's response vary greatly depending on the region and age. Therefore, in the absence of detailed background data, the simple serological diagnosis is not accurate, has no diagnostic significance. ELISA is a sensitive and specific diagnostic method compared to Widal reaction, literatures showed the superiority of ELISA in detecting antibody, and it is suggested that ELISA can replace Widal reaction to monitor serum antibody. At present, there are some commercially available antibody detection kits in the market, including Tubex test, Typhidot/Typhidot-M, IgM Dipstick, all of which aim to detect IgM, but also have the common disadvantage of serological methods, that is, strong cross-reaction. Therefore, serological detection is still controversial for the antigens currently used, and it is necessary to search for specific antigens. In addition to bacterial isolation, culture and serological detection, nucleic acid detection is widely recognized as that most sensitive and specific diagnostic method. The greatest advantage of nucleic acid detection by PCR is that when the culture result is negative, PCR magnifies the small amount of nucleic acid fragments and catches the trace of bacteria. However, the PCR method has some defects, firstly, it is easy to be contaminated; secondly, the abuse of antibiotics aggravates the decrease of the number of bacteria in blood and increases the difficulty of preparing the sample DNA template; thirdly, since more than 90% of the *Salmonella* genomes are similar with only individual base differences, the current PCR is multiplex PCR, but such a complex amplification could have done better in the discovery of more unique genes in the genome.

Accurate diagnosis, though, is essential to ensure that those affected receive timely medical care and appropriate treatment. However, in view of the unique challenges of *salmonella* organisms, new diagnostic tools that aim to be cost-effective and provide accurate results quickly have been developed internationally for several years. At the 11th International Conference on Typhoid and Other *Salmonellosis* in 2020, a new approach to replace clinical monitoring by monitoring the number of *Salmonella* pathogens in the environment was proposed. Therefore, it is particularly important to develop a rapid, efficient and convenient method for the detection of *Salmonella typhi*.

SUMMARY

In order to overcome the defects of the prior art, a first object of the present disclosure is to provide a detection kit for *Salmonella typhi*, which has high sensitivity, high specificity and rapid visualization.

A second object of the present disclosure is to provide a preparation method of the *Salmonella typhi* detection kit, which is simple, rapid and applicable for industrial production.

A third object of the present disclosure is to provide an application of a detection kit for *Salmonella typhi*, and the detection kit for *Salmonella typhi* is used for nucleic acid detection of *Salmonella typhi* to realize rapid visual detection.

The first object of the present disclosure can be achieved by adopting the following technical scheme: a detection kit for *Salmonella typhi* includes amplification primers, crRNA, LbCas12a-RR protein and a single-stranded DNA reporting system;

The crRNA is a specific crRNA targeting to the flag gene of *Salmonella typhi*;

A LbCas12a-RR protein expression sequence is a prokaryotic codon optimized with a Cas12 protein nucleic acid sequence, and amino acid positions of 532 and 595 are mutated into G532R and K595R, respectively.

Further, the amplification primers include flag-RPA-F2 and flag-RPA-R1, a sequence of flag-RPA-F2 is shown as SEQ ID NO. 1, and a sequence of flag-RPA-R1 is shown as SEQ ID NO. 2.

Further, the crRNA includes flag-crRNA1 and flag-crRNA3; a sequence of flag-crRNA1 is shown as SEQ ID No. 3, and a sequence of flag-crRNA3 is shown as SEQ ID No. 4.

Further, the single-stranded DNA reporter system includes a single-stranded DNA FQ reporter, which is a single-stranded DNA labeled with 6-carboxyfluorescein and a fluorescence quencher, and a labeled product is: /56 FAM/TTATTT/3BHQ1/.

The second object of the present disclosure can be achieved by adopting the following technical scheme: a method for preparing a *Salmonella typhi* detection kit, the detection kit includes amplification primers, crRNA, LbCas12a-RR protein and a single stranded DNA reporting system, and the preparation method includes:

Preparing amplification primers step: designing amplification primers containing crRNA;

Preparing crRNA step: aiming at the flag gene of *Salmonella typhi*, searching target sequence including LbCas12a-RR recognition sequence TTTN or/and the TCTN, designing and preparing crRNA;

Preparing LbCas12a-RR protein step: performing prokaryotic codon optimization on the nucleic acid sequence of Cas12 protein, and mutating amino acid positions 532 and 595 into G532R and K595R, respectively, to obtain an expressed sequence of LbCas12a-RR protein; and then constructing into a pET28a expression vector, low temperature inducing soluble protein expression, affinity purifying and molecular sieve purifying to obtain LbCas12a-RR protein.

Further, a length of the amplification primers is 30-37 bp.

Further, in the step of preparing crRNA, a length of crRNA is 23 bp.

The third object of the present disclosure can be achieved by adopting the following technical scheme: an application of a *Salmonella typhi* detection kit, the detection kit of *Salmonella typhi* is used for nucleic acid detection of *Salmonella typhi*; the detection kit includes amplification primers, crRNA, LbCas12a-RR protein and a single-stranded DNA reporting system;

Nucleic acid detection of *Salmonella typhi* includes:

Amplification step: adding amplification primers into a recombinant enzyme polymerase amplification technology system to amplify nucleic acid of a sample to be detected to obtain an amplification product;

Detection step: adding the amplification product into a detection system comprising crRNA, LbCas12a-RR protein and the single-strand DNA report system and reacting to obtain a detection product, and detecting the detection product by a fluorescence detection method to obtain a result.

Further, in the amplification step, amplifying for 30 min at a temperature of 37° C. to obtain the amplification product, and in the detection step, reacting at 37° C. for 25 min to obtain the detection product.

Further, in the detection step, the fluorescence detection method is that, measuring fluorescence value of the detection reaction by using a microplate reader, and setting detection excitation light to 485-520 nm, or observing detection product directly under a light source of 485 nm wavelength.

The design principle of the present disclosure is as follows:

Crispr-Cas (Clustered regularly interspaced short palindromic repeats, CRISPRs) is an adaptive immune system in bacteria, in which Cas protein is targeted to degrade foreign nucleic acids by RNA-guided nucleases. Crispr-Cas12a, in the second family of Cas enzymes, is used to direct RNA-directed cleavage of a single RuvC catalytic domain by double-stranded DNA. The Cas12 enzyme recognizes spacer region adjacent motifs (PAM) rich in thymine (T) nucleotides, catalyzes the maturation of their own guiding CRISPR RNA (crRNA), and specifically recognizes and cleaves complementary paired double-stranded DNA (dsDNA). When the CRISPR Cas12 protein recognizes cleaved target double-stranded DNA in a sequence-specific manner, it can induce strong non-specific single-stranded DNA (ssDNA) trans-cleavage activity, and the fluorescent reporter coupled to ssDNA produces a fluorescent signal upon cleavage. In accordance with that above characteristic of Cas12, the kit provided by the present disclosure can rapidly and accurately detect the nucleic acid of *Salmonella typhi* in clinical samples.

Compared with the prior art, the advantageous effect of the present disclosure is:

1. The detection kit of the present disclosure has high sensitivity, high specificity and rapid visualization, and can be used for rapid detection of *Salmonella typhi* nucleic acid;

2. The detection kit crRNA of the present disclosure recognizes specific PAM sequences according to the characteristics of LbCas12a-RR, the specific crRNA designed on the flag gene target sequence has high specificity;

3. The LbCas12a-RR protein expression sequence of the detection kit of the present disclosure is optimized and mutated to recognize TCTN targeting sequences other than TTTN.

4. The application of the detection kit of the present disclosure can realize direct visual detection with naked eyes under fluorescent lamp, and can realize convenient and quick result interpretation. The detection is accurate, rapid and simple, and can be used for rapid detection, identification and diagnosis of *Salmonella typhi* in basic experiments and clinical frontline.

5. The application mode of the detection kit of the present disclosure is high in specificity, short in time and high in flux, and does not depend on large experimental equipment.

DETAILED DESCRIPTION OF THE EMBODIMENTS

The present disclosure will be further described below with reference to the accompany drawings and specific embodiments:

A detection kit for *Salmonella typhi* includes: amplification primers, crRNA, LbCas12a-RR protein and a single-stranded DNA reporter system;

The amplification primers include flag-RPA-F2 and flag-RPA-R1, a sequence of flag-RPA-F2 is shown as SEQ ID No. 1, and a sequence of flag-RPA-R1 is shown as SEQ ID No. 2;

crRNA is specific to the detection segment of the flag gene of *Salmonella typhi*, crRNA includes flag-crRNA1 and flag-crRNA3 (mixed in equal proportions), a sequence of flag-crRNA1 is shown as SEQ ID NO. 3, and a sequence of flag-crRNA3 is shown as SEQ ID NO. 4;

The expression sequence of LbCas12a-RR protein is obtained by optimizing the prokaryotic codon with a nucleic acid sequence of Cas12 protein (using conventional software) and the 532 and 595 amino acids are mutated into G532R and K595R, respectively.

The single-stranded DNA reporting system includes a single-stranded DNA FQ reporter which is a single-stranded DNA labeled with 6-carboxyfluorescein (6-FAM) and a fluorescence quencher (BHQ1), and the labeled product is: /5 6 FAM/TTTATT/3BHQ1/, Named ssDNA FQ reporter/56FAM/TTTATT/3BHQ1/.

The method for preparing the *Salmonella typhi* detection kit includes:

Preparing amplification primers step: amplification primers contain crRNA were designed, a length of the amplification primers was 30-37 bp;

Preparing crRNA step: aiming at the flag gene (sequence SEQ ID No. 5) of *Salmonella typhi*, a targeting sequence including LbCas12a-RR recognition sequence (PAM) TTTN and TCTN was searched, and a 23 bp crRNA was designed and prepared;

Preparing LbCas12a-RR protein step: the prokaryotic codon optimized on the nucleic acid sequence of the Cas12 protein was performed, and the amino acid positions 532 and 595 were mutated into G532R and K595R, respectively, to obtain a LbCas12a-RR protein expression sequence, as shown in SEQ ID NO. 6, Lbcas12a-RR protein was modified to recognize both TTTN and TCTN, and then constructed into the pET28a expression vector to induce soluble protein expression at low temperature, affinity purified and molecular sieve purified to obtain LbCas12a-RR.

The application of the detection kit for *Salmonella typhi* is that the detection kit for *Salmonella typhi* is used for nucleic acid detection of *Salmonella typhi*, and the detection step is shown in FIG. 1, including:

Amplification step: amplification primers were added into a recombinant enzyme polymerase amplification technology (RPA) system to amplify nucleic acid of a sample to be detected under the condition 37° C., 30 min, to obtain an amplification product.

Detection step: the amplification product was added into the CRISPR Cas12a detection system (the CRISPR Cas12a detection system included crRNA, LbCas12a-RR protein and single-stranded DNA report system) and reacted at a temperature of 37° C. and a reaction time of 25 minutes to get a detection product. Fluorescence detection method was used to obtain the results. Wherein the microplate reader was used to measure the fluorescence value of the detection reaction in the fluorescence detection method, and the detection excitation was set to 485-520 nm; Or the detection product was placed under a light source with a wavelength of 485 nm for direct observation.

When fluorescence detection was employed, if *Salmonella typhi* nucleic acid was present in the detection system, the nucleic acid endonuclease activity of LbCas12a RR protein will be specifically activated by *Salmonella typhi* specific crRNA. ssDNA FQ reporter labeled with a fluorophore and a quenching group was cleaved by activated LbCas12a-RR protein, thereby releasing the activated fluorophore, and a fluorescence reading was detectable by using a microplate reader or a visible green reaction could be seen. Correspondingly, when there is no *Salmonella typhi* nucleic acid in the sample to be tested, there will be no fluorescent reading or no green reaction visible to the naked eye.

Example 1

Nucleic Acid Preparation of *Salmonella typhi:*

The amplification primers were designed according to the sequence of NCBI CMCC50071 strain and synthesized by Nanjing Kingsrui Company, named as flag-PCR-F and flag-PCR-R, corresponding to SEQ ID NO. 7 and SEQ ID NO. 8.

The specific operation for the reparation of DNA nucleic acid samples corresponding to the flag gene of *Salmonella typhi* by PCR was as follows: a standard strain of *Salmonella typhi* (CMCC50071) was obtained from the Center of Disease Control, the strain was subjected to resuscitation amplification, and the bacterial genomic DNA was extracted using the bacterial genomic DNA extraction kit (TIANGEN). Phanta® Max Super-Fidelity DNA Polymerase (Vazyme P505), using the genomic DNA of *Salmonella typhi* as a template to amplify the DNA sample of the corresponding flag gene pcS.*Typhi*-flag. MEG Aclear kit (Thermo Fisher Scientific) was used to purify; DNA quality and concentration were tested and stored at −20° C. until use.

Example 2

Preparation and Detection of crRNA Kit:

According to the targeting sequence of LbCas12a-RR recognizing specific PAM TTTN and TCTN, 20 specific crRNAs were designed on the flag gene target sequence, and the sequence is shown in Table 1:

TABLE 1

Design sequence of crRNA

| SEQ ID NO. | crRNA name | Sequence |
|---|---|---|
| SEQ ID NO. 3 | flag-crRNA1 | TCTGCGAATGGTACTAACTCCCAGTCT |
| SEQ ID NO. 9 | flag-crRNA2 | TCTTTTAAATCAATATCGATAGTTTCA |
| SEQ ID NO. 4 | flag-crRNA3 | TTTAAAAGAAATCAGCTCTAAAACACT |
| SEQ ID NO. 10 | flag-crRNA4 | TTTTAGAGCTGATTTCTTTTAAATCAA |
| SEQ ID NO. 11 | flag-crRNA5 | TTTGTCTTCCGGTCTGCGTATCAAC |
| SEQ ID NO. 12 | flag-crRNA6 | TTTTACCGCGAACATCAAAGGTCTGAC |
| SEQ ID NO. 13 | flag-crRNA7 | TTTCACGCCGTTGAACTGAGTCTGGCC |
| SEQ ID NO. 14 | flag-crRNA8 | TTTTAGCAGTAATTGCACCTGTTTTCT |
| SEQ ID NO. 15 | flag-crRNA9 | TTTGAGCAACGCCAGTACCATCTGTAT |

TABLE 1-continued

Design sequence of crRNA

| SEQ ID NO. | crRNA name | Sequence |
| --- | --- | --- |
| SEQ ID NO. 16 | flag-crRNA10 | TCTGCGCAATGGAGATACCGTCGTTAG |
| SEQ ID NO. 17 | flag-crRNA11 | TCTCCATTGCGCAGACCACTGAAGGCG |
| SEQ ID NO. 18 | flag-crRNA12 | TCTGACCTCGACTCCATCCAGGCTGAA |
| SEQ ID NO. 19 | flag-crRNA13 | TCTGGCCGGATACACGGTCGATTTCGT |
| SEQ ID NO. 20 | flag-crRNA14 | TCTGGGCTGTAATAGGATCTGTACCAT |
| SEQ ID NO. 21 | flag-crRNA15 | TCTGTATAAGTAGTGGTTTTAGCAGTA |
| SEQ ID NO. 22 | flag-crRNA16 | TTTGCGCCACCAAATTTCACAGCTCCA |
| SEQ ID NO. 23 | flag-crRNA17 | TTTGGTGGCGCAAATGGTAAATCTGAA |
| SEQ ID NO. 24 | flag-crRNA18 | TTTGTCAAGGTCGCTTGCTAAGTAAGT |
| SEQ ID NO. 25 | flag-crRNA19 | TTTAAGCTCACCGCCTGTTCTGAAGTT |
| SEQ ID NO. 26 | flag-crRNA20 | TTTCTGCAGTGGGTTTTCAGTCTTATC |

The effect of flag-crRNA1 to flag-crRNA20 were detected in sequence. The CRISPR/Cas12a detection system was set up as shown in Table 2, 1 µL flag-crRNA1 to flag-crRNA20 were added into the system respectively, and the other components were kept consistent, mixed and reacted at 37° C. for 25 minutes to obtain the detection product.

TABLE 2

CRISPR/Cas12a Testing System (20 µL)

| Ingredients | Volume/Sample |
| --- | --- |
| 10*Buffer | 2 µL |
| Rnase Inhibitors (40 U/µL) | 1 µL |
| LbCas12a-RR protein (200 ng/µL) | 1 µL |
| ssDNA FQ reporter (25 pmol/µL) | 1 µL |
| crRNA (1 nM/µL) | 1 µL |
| DNA nucleic acid sample | 1 µL |
| H$_2$O (RNA free) | The total amount of the system was added to 20 µL |

Figure 1:
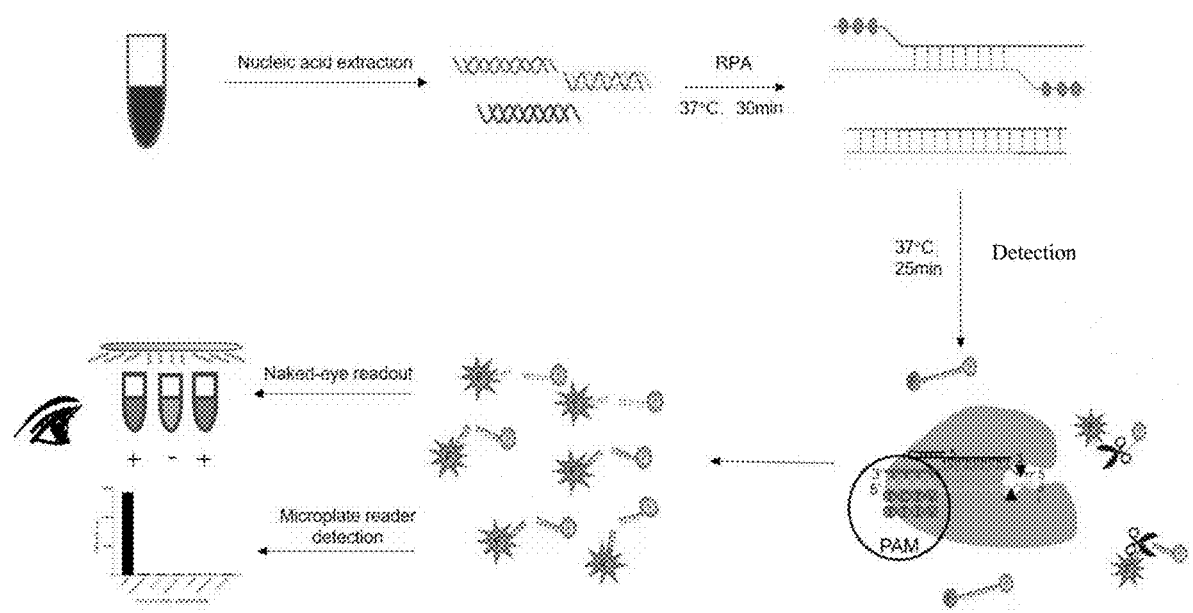
FIG. 1 is a schematic diagram of a detection step.
Figure 2:
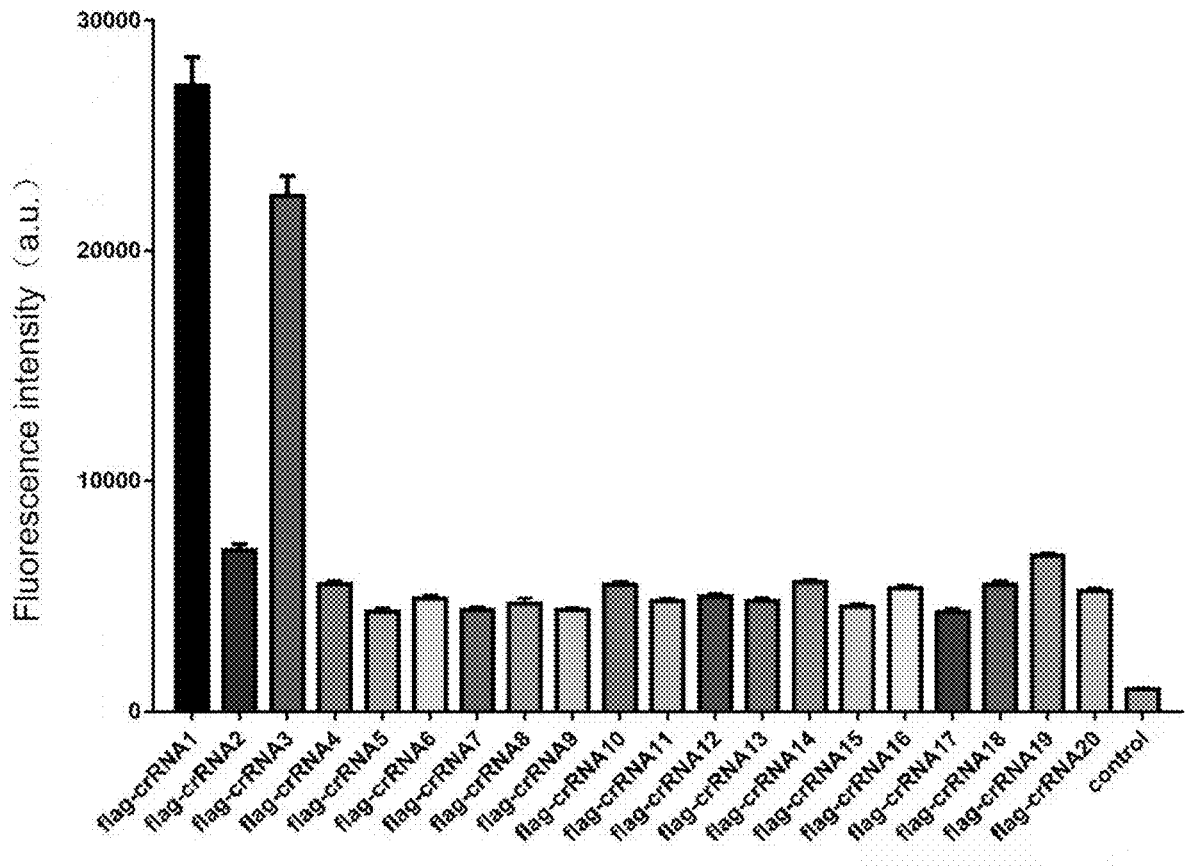
FIG. 2 shows the fluorescence detection results of crRNAs in Example 2 measured by a microplate reader.

The detection activity of CRISPR Cas12a detection system was determined by fluorescence detection. The fluorescence of the detection reaction was measured using a full-wavelength microplate reader, wherein the excitation wavelength was 485 nm, the emission wavelength was 520 nm, and the fluorescence value of the detection for 25 min was read as the reaction value. For *Salmonella typhi* different response, the test results are shown in FIG. 2. The results showed that flag-crRNA1 and flag-crRNA3 could detect the corresponding flag gene fragment efficiently and specifically.

Figure 3:
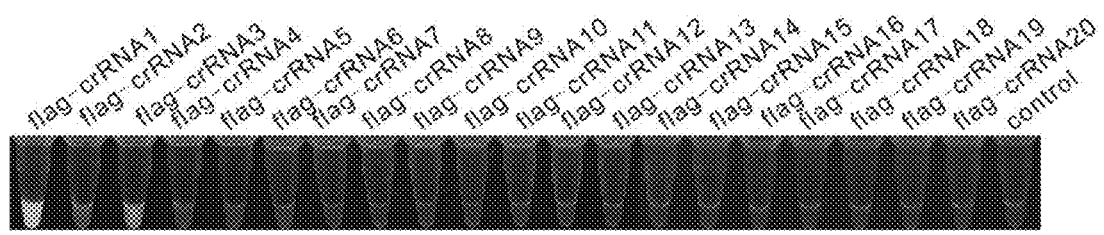
FIG. 3 shows the fluorescence detection results of crRNAs in Example 2 by visual observation.

In addition, the detection product was placed under a laser lamp with a wavelength of 485 nm, and the result could be directly interpreted with the naked eye. When the target nucleic acid fragment was recognized by the crRNA specifically, the color of the reaction product changed from colorless to fluorescent green; correspondingly, if there was no corresponding target nucleic acid to be detected, the color of the reaction product was still colorless. As shown in FIG. 3, the flag-crRNA1 and the flag-crRNA3 can efficiently and specifically detect the corresponding flag gene fragment.

Example 3

The amplification primer of the kit was prepared and detected, and the sequence of the designed amplification primer was shown in Table 3:

TABLE 3

Designed sequence of amplified primers

| SEQ ID NO. | Name of amplification primer | Sequence |
| --- | --- | --- |
| SEQ ID NO. 27 | flag-RPA-F1 | tctccattgcgcagaccactgaaggcgcgctgaa |
| SEQ ID NO. 1 | flag-RPA-F2 | tctccattgcgcagaccactgaaggcgcgctgaacg |
| SEQ ID NO. 28 | flag-RPA-F3 | cctgcagcgtgtgcgtgaactggcggttcag |
| SEQ ID NO. 29 | flag-RPA-F4 | aacctgcagcgtgtgcgtgaactggcggttcag |
| SEQ ID NO. 2 | flag-RPA-R1 | tttcggggtgtaggcatcttggacattaagc |
| SEQ ID NO. 30 | flag-RPA-R2 | gcagtttctttcggggtgtaggcatcttggac |
| SEQ ID NO. 31 | flag-RPA-R3 | tcaacggttacagcagtttcttctcggggtg |
| SEQ ID NO. 32 | flag-RPA-R4 | gcagtttctttcggggtgtaggcatcttggac |

Based on the DNA nucleic acid sample corresponding to the flag gene fragment of *Salmonella typhi*, the molecular weight of the detection fragment was calculated, and a 10-fold gradient dilution was performed to obtain a DNA test sample containing 1*e4 copy number per µL (copy/µL); the amplification primers of Table 3 were added to the recombinant enzyme polymerase amplification technology (RPA) system (as shown in Table 4) respectively to amplify the DNA test sample;

TABLE 4

Recombinase polymerase amplification (RPA) system (25 µL)

| Ingredient | Volume/Sample |
| --- | --- |
| DNA nucleic acid sample | 1 µL |
| ddH$_2$O | 5 µL |
| RPA-F | 1.25 µL |
| RPA-R | 1.25 µL |

TABLE 4-continued

| Recombinase polymerase amplification (RPA) system (25 μL) | |
| --- | --- |
| Ingredient | Volume/Sample |
| Reaction buffer | 15.5 μL |
| Magnesium acetate | 1 μL |

DNA nucleic acid sample, ddH$_2$O, RPA-F, RPA-R and reaction buffer were added into the reaction tube to dissolve and mix, then 1 μL magnesium acetate was added into the reaction tube at 37° C. for 30 min to obtain the amplification product.

Figure 4:
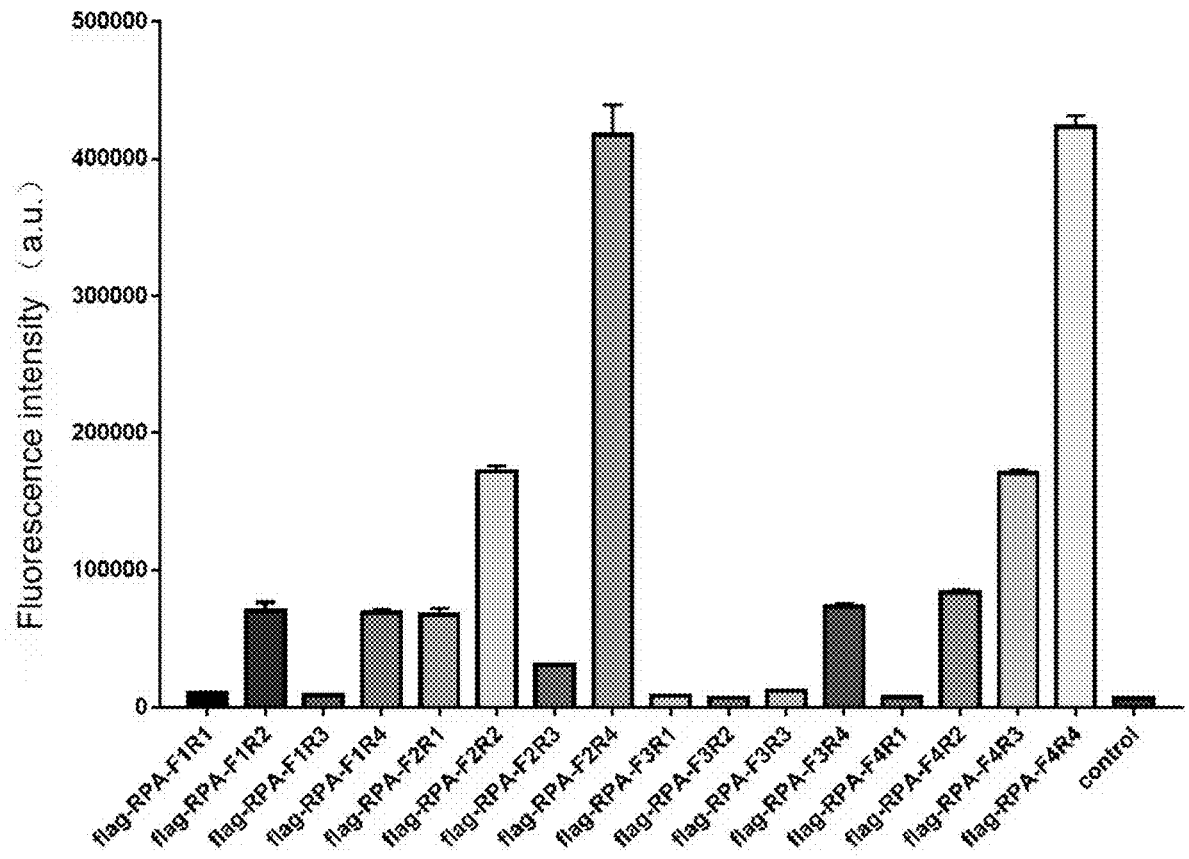
FIG. 4 shows the fluorescence detection results of crRNAs in Example 3 measured by a microplate reader.
Figure 5:
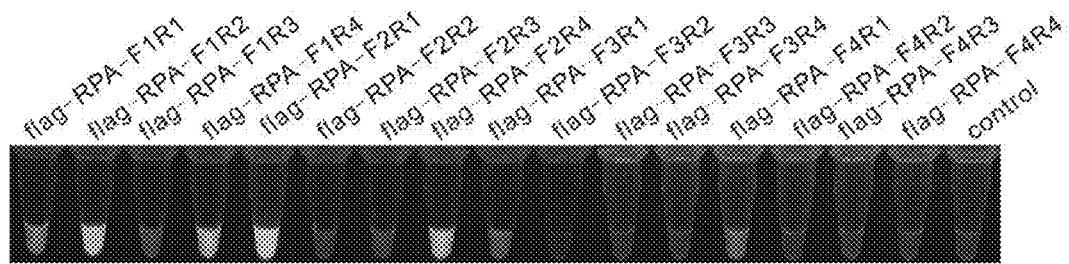
FIG. 5 shows the fluorescence detection results of crRNAs in Example 3 by visual observation.

5 μL isothermal amplification product was added into 20 μL CRISPR Cas12a detection system (<same as Table 2, crRNA was mixed with equal amount of flag-crRNA1 and flag-crRNA3), mix well, and reacted at 37° C. for 30 min for fluorescence result interpretation. The detection activity of the CRISPR Cas2a detection system was determined by fluorescence detection, which was detected by a microplate reader (as shown in FIG. 4) and fluorescent visual inspection (as shown in FIG. 5), respectively. It was found that flag-RPA-F2 and flag-RPA-R1 could efficiently amplify and detect the corresponding flag gene fragment. flag-RPA-F2 and flag-RPA-R1 were selected as amplification primers.

Example 4

Highly sensitive detection of nucleic acid detection of *Salmonella Typhi*:

The molecular weight of the detected fragment was calculated according to the DNA nucleic acid sample corresponding to the flag gene fragment of *Salmonella typhi*, and 10-fold gradient dilution was performed, DNA test samples containing 1*e6, 1*e5, 1*e4, 1*e3, 1*e2, 1*e1 and 1*e0 copy numbers (copy /.mu.L) per μL were obtained.

Amplification step, amplification system as Table 5 shows:

TABLE 5

| Recombinase polymerase amplification (RPA) system (25 μL) | |
| --- | --- |
| Ingredient | Volume/Sample |
| DNA test sample | 1 μL |
| ddH$_2$O | 5 μL |
| flag-RPA-F2 | 1.25 μL |
| flag-RPA-R1 | 1.25 μL |
| Reaction buffer | 15.5 μL |
| Magnesium acetate | 1 μL |

The nucleic acid of the sample was amplified under the condition of 37° C. for 30 min to obtain the amplified product.

Detection step, 5 μL of the amplification product was added into the CRISPR/Cas12a detection system shown in Table 6, and the reaction was carried out under the conditions of temperature 37° C. and reacted for 25 minutes to obtain the detection product.

TABLE 6

| CRISPR/Cas12a Testing System (20 μL) | |
| --- | --- |
| Ingredient | Volume/Sample |
| 10*Buffer | 2 μL |
| Rnase Inhibitors (40 U/μL) | 1 μL |

TABLE 6-continued

| CRISPR/Cas12a Testing System (20 μL) | |
| --- | --- |
| Ingredient | Volume/Sample |
| LbCas12a-RR protein (200 ng/μL) | 1 μL |
| ssDNA FQ reporter (25 pmol/μL) | 1 μL |
| crRNA (1 nM/μL) | 1 μL |
| Amplification product | 5 μL |
| H$_2$O (RNA free) | The total amount added to the system is 20 μL |

Figure 6:
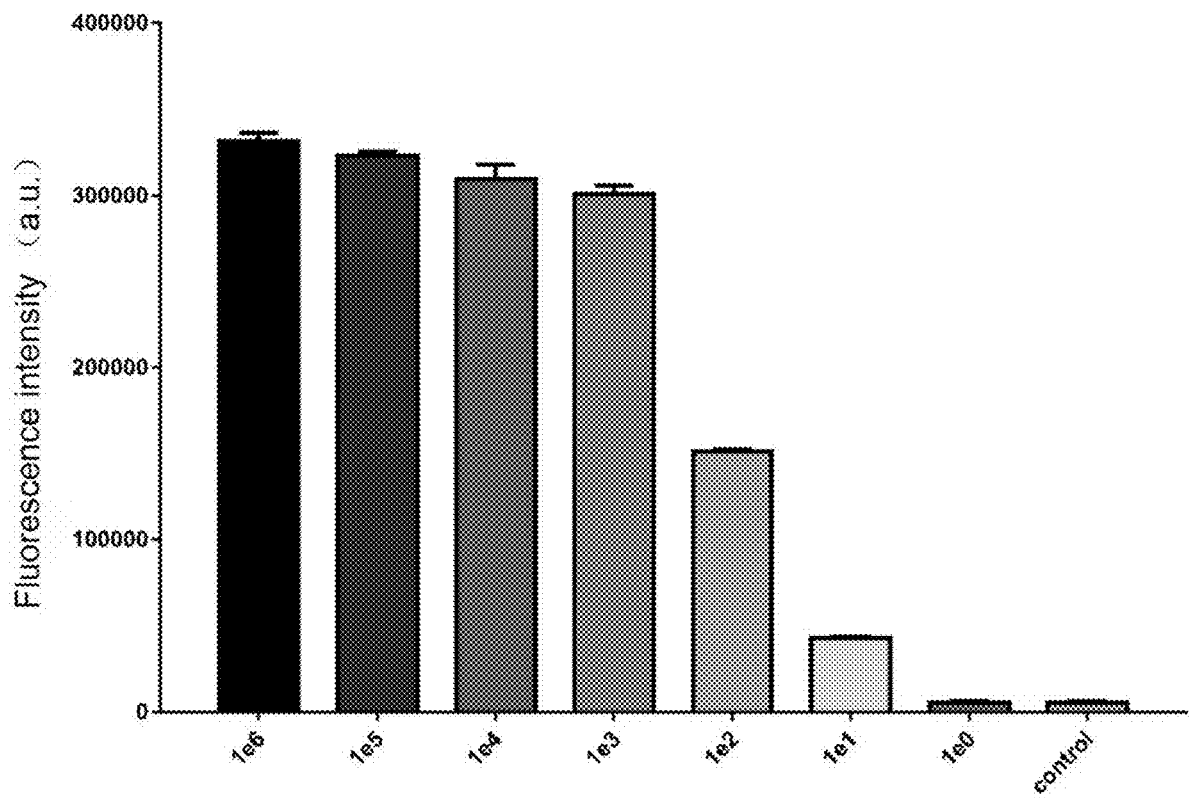
FIG. 6 shows the fluorescence detection results of crRNAs in Example 4 measured by a microplate reader.
Figure 7:
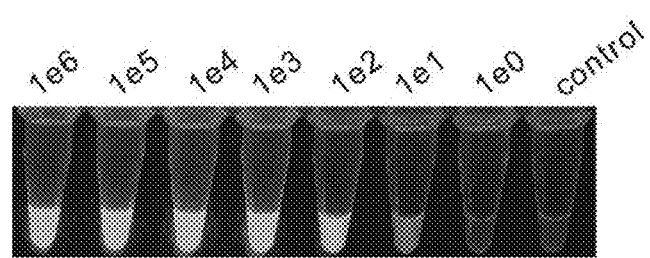
FIG. 7 shows the fluorescence detection results of crRNA in Example 4 by visual observation.

The fluorescence of the reaction was measured with a microplate reader. The fluorescence of the reaction was measured with a full wavelength microplate reader. The excitation wavelength was 485 nm, and the emission wavelength was 520 nm, the fluorescence value of the detection 25 min was read as the reaction value, and the result is shown in FIG. 6. High sensitivity detection of 1*e1 copy of bacterial nucleic acid can be realize, and high sensitivity detection of 1*e1 copy of bacterial nucleic acid can be realized. The detection product was placed in a laser lamp fluorescent visual inspection at wavelength of 485 nm, as shown in FIG. 7, and high sensitivity detection of 1*e1 copy of bacterial nucleic acid can be realized.

Example 5

In order to detect whether that fluorescence detection method is highly specific for *Salmonella typhi* and can effectively distinguish *Salmonella typhi* from other serotype of *Salmonella typhi*, the following tests were carried out.

First, referring to the detection segment pcS. *typhi*-flag for the nucleic acid of *Salmonella typhi* and the method in example 1, DNA samples of corresponding gene sequences of other serotypes of *Salmonella* were prepared: pcS. *typhimurium*-flag, pcS.London-flag, pcS.*Enteritidis*-flag, pcS. Weltevreden-flag and pcS.Derby-flag.

Second, referring to Example 4, a DNA test sample containing 1*e4 copies per μL (copy/μL) was used, and a detection product was obtained through the amplification step and the detection step.

Figure 8:
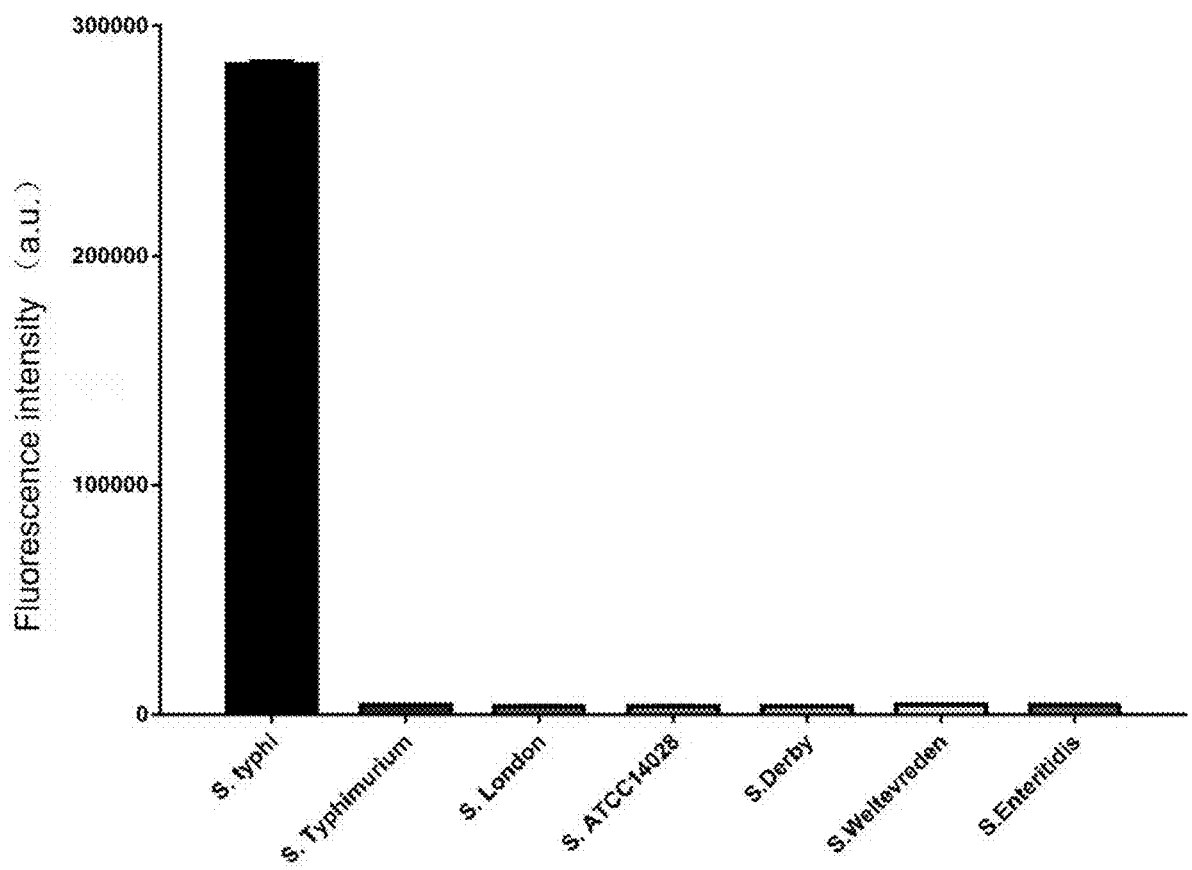
FIG. 8 shows the fluorescence detection results of crRNAs in Example 5 measured by a microplate reader.
Figure 9:
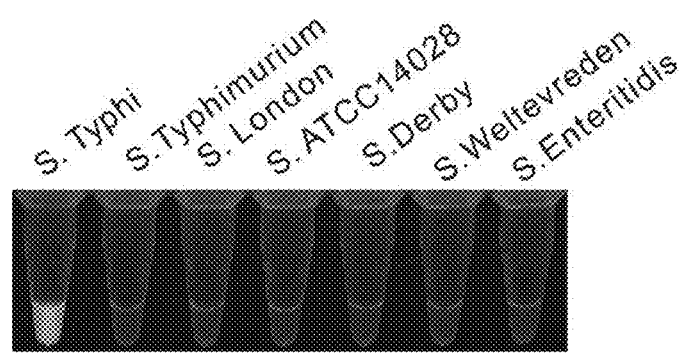
FIG. 9 shows the fluorescence detection results of the crRNA of Example 5 by visual observation.

FIG. 8 shows the results of the detection using the microplate reader, and FIG. 9 shows the results of the direct detection with naked eye, and the fluorescence detection method can detect the nucleic acid of *Salmonella typhi* with high specificity, but does not respond to other serotypes of *Salmonella*.

Example 6

Nucleic acid detection of *Salmonella typhi* in clinically isolated strains of *Salmonella typhi*:

First, a clinically isolated and preserved *Salmonella typhi* strain was resuscitated and amplified, and the bacterial genomic DNA was extracted with the bacterial genomic DNA extraction kit (TIANGEN). 1 u.L of genomic DNA of each clinical strain was subjected to the amplification step and the detection step as in Example 4 to obtain a detection product.

Figure 10:
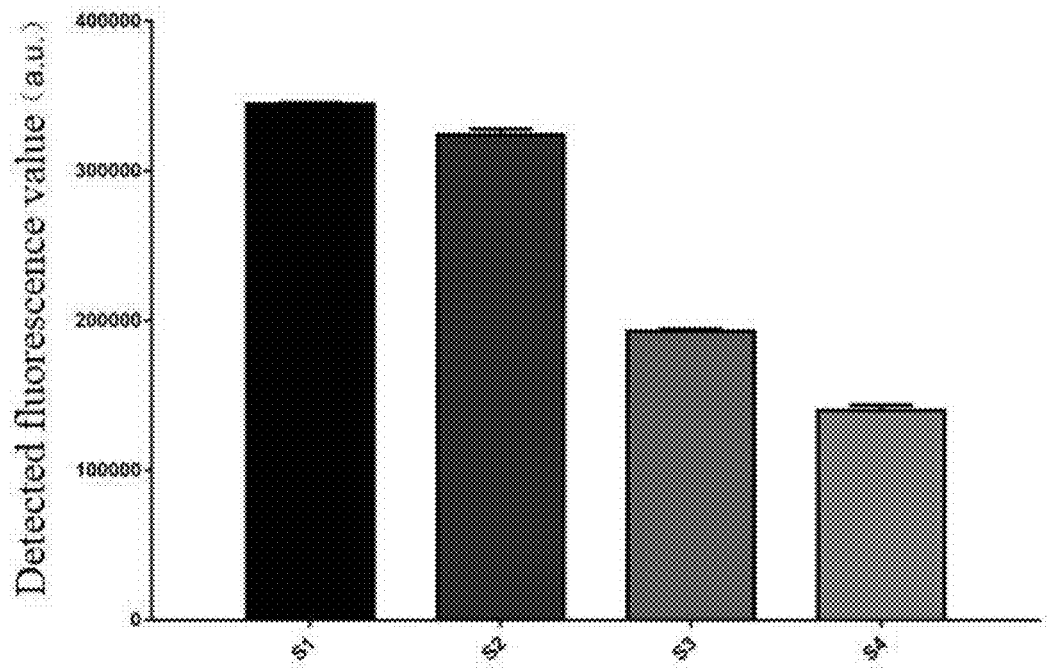
FIG. 10 shows the fluorescence detection results of crRNAs in Example 6 measured by a microplate reader.
Figure 11:
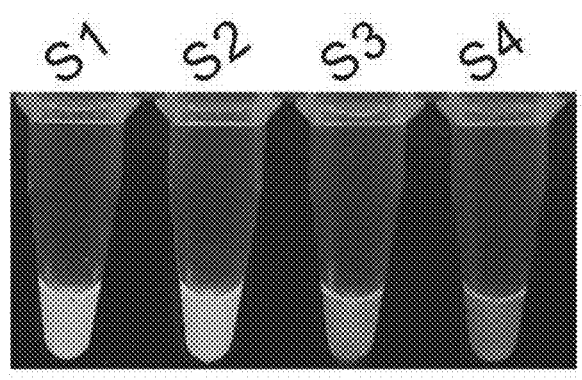
FIG. 11 shows the fluorescence detection results of the crRNA of Example 6 by visual observation.

The results of detection using a microplate reader are shown in FIG. 10, and the results of direct detection with the naked eye are shown in FIG. 11. The fluorescence detection method is effective for the determination of clinically isolated strains.

Those skilled in the art may make various other corresponding changes and modifications according to the technical solutions and concepts described above, and all such changes and modifications should fall within the scope of the claims of the present disclosure.

What is claimed is:

1. A detection kit for detecting *Salmonella typhi*, comprising: amplification primers, a crRNA, a LbCas12a-RR protein and a single-stranded DNA reporter system;
   wherein the LbCas12a-RR protein is encoded by the nucleotide sequence consisting of SEQ ID NO: 6 and is a mutant of a Cas 12a protein from Lachnospiraceae *bacterium* formed by substituting each of Glycine and Lysine at positions 532 and 595 of the Cas12a protein from Lachnospiraceae *bacterium* with Arginine; and
   wherein the crRNA comprises flag-crRNA1 and flag-crRNA3, the flag-crRNA1 consists of SEQ ID No. 3, and the flag-crRNA3 consists of SEQ ID No. 4.

2. The detection kit for detecting *Salmonella typhi* according to claim 1, wherein the amplification primers comprise flag-RPA-F2 and flag-RPA-R1, and the flag-RPA-F2 consists of SEQ ID NO. 1, and the flag-RPA-R1 consists of SEQ ID NO. 2.

3. The detection kit for detecting *Salmonella typhi* according to claim 1, wherein the single-stranded DNA reporting system comprises a single-stranded DNA FQ reporter which is a single-stranded DNA consisting of 5'-FAM-TTTATT-BHQ1-3' wherein FAM is 6-carboxyfluorescein and BHQ1 is Black Hole Quencher 1.

* * * * *